United States Patent [19]

Cooper

[11] Patent Number: 4,468,514

[45] Date of Patent: Aug. 28, 1984

[54] PREPARATION OF 3-BROMOCEPHALOSPORINS FROM THIAZOLINE AZETIDINONES

[75] Inventor: Robin D. G. Cooper, Indianapolis, Ind.

[73] Assignee: Eli Lilly and Company, Indianapolis, Ind.

[21] Appl. No.: 450,707

[22] Filed: Dec. 17, 1982

[51] Int. Cl.$^3$ .............................................. C07D 501/04
[52] U.S. Cl. ........................................ 544/27; 544/16; 544/22; 544/28; 544/30; 544/26
[58] Field of Search ..................... 544/27, 28, 16, 26, 544/21, 22, 30; 424/246

[56] References Cited

U.S. PATENT DOCUMENTS

| | | | |
|---|---|---|---|
| 3,932,398 | 1/1976 | Nudelman et al. | 260/243 C |
| 4,018,776 | 4/1977 | Foglio et al. | 260/243 C |
| 4,091,026 | 5/1978 | Micetich et al. | 260/306.7 C |
| 4,183,855 | 1/1980 | Yoshioka et al. | 260/307 F |

OTHER PUBLICATIONS

Micetich et al., Tetra Letters, 979–982, 1976.

*Primary Examiner*—Nicholas S. Rizzo
*Attorney, Agent, or Firm*—Charles W. Ashbrook; Arthur R. Whale

[57] ABSTRACT

Thiazoline azetidinones are converted in good yield to 3-bromo-3-methylcephams by treatment with a bromine source and dimethyl sulfoxide.

9 Claims, No Drawings

PREPARATION OF 3-BROMOCEPHALOSPORINS FROM THIAZOLINE AZETIDINONES

BACKGROUND OF THE INVENTION

3-Halo-3-methylcephams are known in the art to be useful in the synthesis of 3-methyl-3-cephem antibiotics. Several processes have been developed for the preparation of 3-halo-3-methylcephams. Micetich and Morin, for instance, in *Tetrahedron Letters*, No. 13, pp. 979-982, 1976, disclosed the reaction of a thiazoline azetidinone with iodine and water to give the corresponding 3-iodo-3-methylcepham. These authors reported that the reaction was not general in that bromine and chlorine failed to behave as did iodine.

Foglio et al., in U.S. Pat. No. 4,018,776, report an iodination process comprising reaction of a thiazoline azetidinone with iodine in the presence of a heavy metal oxide or a free radical initiator such as a peroxide. Nadelman et al., in U.S. Pat. No. 3,932,398, disclose the reaction of a penicillin sulfoxide with a neutral or basic catalyst in a polyhaloalkane solvent to give a 3-halo-3-methylcepham. More recently, Yoshioka et al., in U.S. Pat. No. 4,183,855, disclosed the synthesis of certain 3-halo-3-methyl-1-oxacephams from oxazoline azetidinone derivatives.

An object of this invention is to provide a new process for preparing 3-bromo-3-methylcephams.

SUMMARY OF THE INVENTION

This invention concerns a process for converting thiazoline azetidinones to 3-bromocephams. The invention more particularly provides a method for preparing a 3-bromocepham compound of the formula

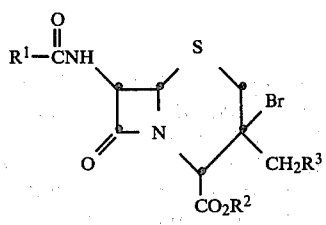

wherein $R^1$ is an organic radical, $R^2$ is a carboxy protecting group, and $R^3$ is hydrogen, bromo, chloro, acetoxy, alkylthio, or arylthio, comprising reacting a thiazoline azetidinone of the formula

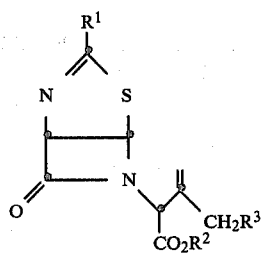

with a bromine source and dimethyl sulfoxide at a temperature of about 0° C. to about 50° C.

The process is preferably carried out employing a thiazoline azetidinone wherein $R^1$ is phenoxymethyl, phenylmethyl, 2-thienylmethyl, chloromethyl, α-formyloxyphenylmethyl, or α-acetamidophenylmethyl; $R^2$ is p-nitrobenzyl, 2,2,2-trichloroethyl, methyl or diphenylmethyl; and $R^3$ is hydrogen or chloro.

DETAILED DESCRIPTION OF THE INVENTION

In the above formulas, $R^1$ defines "an organic radical". This term means a monovalent group of an acyl residue of a carboxylic acid, less the acyl carbonyl moiety. $R^1$ is the monovalent organic radical resulting from the diminution of the carbonyl function of an acyl group derived from a carboxylic acid. These $R^1$ groups are well known in the cephalosporin art, and no novelty is asserted herein regarding the groups defined by $R^1$. Typical $R^1$ organic radicals contemplated herein include (a) $C_1$-$C_7$ alkyl, cyanomethyl, $C_1$-$C_6$ haloalkyl, 4-protected amino-4-protected carboxybutyl; or (b) $C_1$-$C_6$ alkoxy, phenoxy, benzyloxy or 4-methoxybenzyloxy; or (c) the group —$R^4$ wherein $R^4$ is phenyl or substituted phenyl wherein the substituents are 1 or 2 halogens, protected hydroxy, cyano, trifluoromethyl, $C_1$-$C_4$ alkyl, $C_1$-$C_4$ alkoxy, protected carboxy, protected carboxymethyl, protected hydroxymethyl, protected aminomethyl, or a bicyclic aryl groups such as naphthyl, benzothienyl, substituted naphthyl or substituted benzothienyl; or (d) an arylalkyl group of the formula $R^4$—(O)-$_m$—$CH_2$— wherein $R^4$ is as defined above, and m is 0 or 1; or (e) a substituted arylalkyl group of the formula

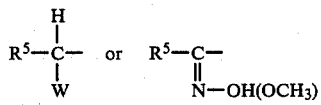

wherein $R^5$ is $R^4$ as defined above, 1-thienyl, 3-thienyl, 2-protected aminothiazol-4-yl, 2-furyl or 3-furyl; W is protected hydroxy, protected carboxy, protected amino, or (f) a heteroarylmethyl group of the formula $R^6$—$CH_2$— wherein $R^6$ is 2-thienyl, 3-thienyl, 2-protected aminothiazol-4-yl, 2-furyl, 3-furyl, 2-thiazolyl, 5-tetrazolyl, 1-tetrazolyl.

$R^2$ in the above formula is a carboxy protecting group.

$R^3$ in the above formula is hydrogen, chloro, acetoxy, alkylthio such as methylthio or tert.-butylthio, or arylthio such as phenylthio, tetrazolylthio, thiadiazolylthio and the like.

In the foregoing definitions, the term "$C_1$-$C_7$ alkyl" refers to methyl, ethyl, n-propyl, n-butyl, isobutyl, pentyl, n-hexyl, cyclohexyl, n-heptyl and like aliphatic hydrocarbon chains.

The term "$C_1$-$C_6$ haloalkyl" refers to chloromethyl, bromomethyl, iodomethyl, 2-bromoethyl, 2-chloroethyl, 2-bromopropyl, 2-iodopropyl, 2-chlorobutyl, 2-bromo-2-methylpropyl, 2-bromobutyl, 2-bromo-2-methylbutyl and like groups.

In the following specification, the protecting group designation is omitted for simplicity in nomenclature, but it is understood that, in the description of the process of this invention, each carboxy, hydroxy or amino group is to be a protected group.

The term "protected amino" as employed in the above definition has reference to an amino group substituted with one of the commonly employed amino blocking groups such as the tert-butoxycarbonyl group (t-BOC), the benzyloxycarbonyl group, the 4-methoxybenzyloxycarbonyl group, the 2,2,2-trichloroethoxycarbonyl group, the dimethyl-tert.-butylsilyl group, and like amino protecting groups. The nature of such amino protecting groups. The nature of such amino protecting groups is not critical so long as the protected amino functionality is stable under the reaction conditions described hereinafter.

The term "protected hydroxy" has reference to any group stable under the reaction conditions of the subsequent step in this synthesis of the 3-bromo-3-methylcepham compounds, but readily cleavable thereafter. Such groups include the formyloxy group, the chloroacetoxy group, the benzhydryloxy group, the β-trimethylsilylethyloxy group, the dimethyl-tert.-butylsilyl group, and the like.

The term "carboxy protecting group" or "protected carboxy" has reference to a carboxy group which has been esterified with one of the commonly used carboxylic acid protecting ester groups employed to block or protect the carboxylic acid functionality while reactions involving other functional sites of the molecule are carried out. Such protected carboxy groups are noted for their ease of cleavage by hydrolytic methods to the corresponding carboxylic acid. Examples of carboxylic acid protecting groups include tert-butyl, methyl, cyanomethyl, p-methoxybenzyl, diphenylmethyl, 2,4,6-trimethylbenzyl, 2,2,2-trichloroethyl, and like ester forming moieties. The nature of such ester forming groups is not critical so long as the ester formed therewith is stable under the reaction conditions described hereinafter. Preferred carboxylic acid protecting groups are diphenylmethyl, 4-methoxybenzyl, and p-nitrobenzyl.

In the foregoing definitions, hydroxy, amino, and carboxy protecting groups are not exhaustively defined. The function of such groups is to protect the reactive functional groups during the preparation of the desired products and then to be removed without disrupting the remainder of the molecule. Many such protecting groups are well known in the art and the use of other groups equally applicable to the process and compounds of the present invention, such as those described in J. F. W. McOmie, "Protective Groups in Organic Chemistry", Plenum Press, 1973, will be recognized as suitable. Thus, there is no novelty or inventiveness asserted with regard to the "protecting groups" alluded to in this specification.

When in the above definition $R^4$ represents a substituted phenyl group, $R^4$ can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or dihydroxyphenyl group such as 4-hydroxyphenyl, 3-hydroxyphenyl, 2,4-dihydroxyphenyl (where all hydroxy groups are protected) and the like; a cyanophenyl group, for example 4-cyanophenyl; a mono or disubstituted lower alkylphenyl group such as 4-methylphenyl, 2,4-dimethylphenyl, 2-methylphenyl, 4-isopropylphenyl, 4-ethylphenyl, 3-n-propylphenyl and the like; a mono or disubstituted lower alkylphenyl ether for example, 2,6-dimethoxyphenyl, 4-methoxyphenyl, 3-ethoxyphenyl, 4-isopropoxyphenyl, 4-tert-butoxyphenyl, 3-ethoxy-4-methoxyphenyl and the like. Also, $R^4$ represents disubstituted phenyl groups wherein the substituents can be different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and like disubstituted phenyl groups bearing different substituents.

It will be noted that the process of this invention converts a thiazoline azetidinone to a cephalosporin derivative having an organic acyl group defined as

attached to the 7-amino group.

Illustrative of the acyl groups,

where $R^1$ is $C_1-C_7$ alkyl, or $C_1-C_6$ haloalkyl, are acetyl, propionyl, butyryl, hexanoyl, chloroacetyl, bromoacetyl and the like.

Representative of the acyl groups

when $R^1$ is phenyl or substituted phenyl are benzoyl, 2,6-dimethoxybenzoyl, 4-chlorobenzoyl, 4-methylbenzoyl, 3,4-dichlorobenzoyl, 4-cyanobenzoyl, 3-bromobenzoyl, 3-protected aminobenzoyl.

Illustrative of the acyl groups

when $R^1$ is a group of the formula $R^4-(O)_m-CH_2-$, m is 0 and $R^4$ is phenyl or substituted phenyl, are phenylacetyl, 4-chlorophenylacetyl, 3-protected hydroxyphenylacetyl, 3-cyanophenylacetyl, 4-acetoxy-3-methylphenylacetyl, 4-bromophenylacetyl, 4-ethoxyphenylacetyl, 3,4-dimethoxyphenylacetyl and the like; and when m is 1, representative groups are phenoxyacetyl, 3-hydroxyphenoxyacetyl, 4-chlorophenoxyacetyl, 3,4-dichlorophenoxyacetyl, 2-chlorophenoxyacetyl, 4-methoxyphenoxyacetyl, 2-ethoxyphenylacetyl, 3,4-dimethylphenoxyacetyl, 4-isopropylphenoxyacetyl, 3-cyanophenoxyacetyl and like substituted phenoxyacetyl groups.

Illustrative of the acyl groups when $R^1$ is a substituted arylalkyl group of the formula

are the carboxy substituted acyl groups such as the 2-carboxy-2-phenylacetyl group of the formula

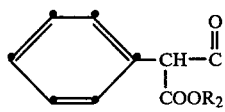

and similar groups wherein the phenyl ring is substituted, for example, 2-carboxy-2-(4-chlorophenyl)acetyl, 2-carboxy-2-(4-methoxyphenyl)acetyl, 2-carboxy-2-(2-thienyl)acetyl, 2-carboxy-2-(4-methylphenyl)acetyl, 2-carboxy-2-(4-(carboxymethyl)phenyl)acetyl, 2-carboxy-2-(4-(formyloxymethyl)phenyl)acetyl and like groups.

Representative of the acyl groups when R¹ is a hydroxy substituted arylalkyl group are 2-hydroxy-2-(4-methoxyphenyl)acetyl, 2-hydroxy-2-(3-chloro-4-hydroxyphenyl)acetyl, 2-hydroxy-2-(3-bromophenyl)acetyl, 2-hydroxy-2-(3,5-dichloro-4-hydroxyphenyl)acetyl, 2-hydroxy-2-(3-chloro-4-methoxyphenyl)acetyl, 2-hydroxy-2-(3-chlorophenyl)acetyl, 2-hydroxy-2-(4-aminomethylphenyl)acetyl, 2-hydroxy-2-(3-thienyl)acetyl; (wherein all hydroxy groups bear a hydroxy protecting group during the process of the invention).

When R¹ is an amino substituted arylalkyl group, acyl groups represented thereby include 2-amino-2-phenylacetyl, 2-amino-2-(4-cyanophenyl)acetyl, 2-amino-2-(4-hydrophenyl)acetyl, and like groups.

Representative of the acyl group

when R¹ is a heteroarylmethyl group of the formula R⁶—CH₂— are 2-thienylacetyl, 3-thienylacetyl, 2-furylacetyl, 2-thiazolylacetyl, 1-tetrazolylacetyl, 5-tetrazolylacetyl and the like.

In the above formulas, R³ defines hydrogen, bromo, chloro, acetoxy, alkylthio or arylthio. The term arylthio includes groups such as phenylthio as well as a heterocyclic ring system selected from

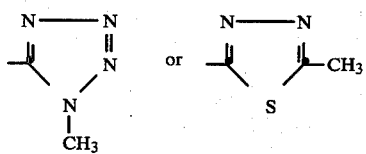

attached through a sulfur atom.

According to the process provided by this invention, a thiazoline azetidinone is reacted with a bromine source in dimethyl sulfoxide. The term "bromine source" means any compound containing bromine that is capable of being oxidized by dimethyl sulfoxide to provide Br+ or its equivalent. Numerous bromine containing compounds are known to be subject to oxidation by dimethyl sulfoxide. Nace and Monagle, for instance, described the oxidation of primary alkyl halides by dimethyl sulfoxide to give aldehydes, and halide+ as a biproduct; *J. Org. Chem.*, 24, 1792 (1959). Any such primary alkyl bromides can be employed in the present process; all that is required is that Br+ cations be generated so as to react with the thiazoline azetidinone. Typical compounds to be employed as bromine sources according to this invention include liquid bromine (i.e. Br₂); hydrogen bromide; alkenyl bromides such as allyl bromide; arylalkyl bromides such as phenylmethyl bromide, 2-phenylethyl bromide, 2-naphthylethyl bromide and the like; aroylalkyl bromides such as benzoylmethyl bromide, 4-methylbenzoylmethyl bromide, 2-(4-bromobenzoyl)ethyl bromide, and the like. Preferred bromine sources include liquid bromine (Br₂), benzoylmethyl bromide and hydrobromic acid.

The process of the invention generally is carried out employing dimethyl sulfoxide in excessive amounts so as to function as reactant and as solvent. Other solvents can be employed if desired, however, for instance in conjunction with dimethyl sulfoxide. Typical of other solvents that can be employed include water, toluene, N,N-dimethylformamide, dichloromethane, benzene, xylene, and the like. When such co-solvents are employed, the dimethyl sulfoxide is present in the reaction mixture in about a one molar excessive amount relative to the thiazoline azetidinone. The best mode contemplated for the process is to employ dimethyl sulfoxide as both reactant and solvent. Another preferred solvent system is a mixture of dimethylsulfoxide and water.

The bromine source, for example a compound such as liquid bromine or benzoylmethyl bromide, generally is employed in approximately equimolar amounts relative to the thiazoline azetidinone. If desired, however, excessive amounts ranging from about 1 to about 10 molar excess can be employed without adverse consequences.

The process generally is carried out at a temperature of about 0° to about 50° C. A preferred embodiment of the invention comprises carrying out the reaction at a temperature of about 20° to about 30° C., idealy about room temperature of approximately 24° C.

The process of the invention appears to be improved in some instances by the addition of an acid to the reaction mixture. Typical acids that can be utilized include p-toluenesulfonic acid (generally as the monohydrate), acetic acid, hydrobromic acid and the like. When such an acid is employed, it generally will be present in a catalytic amount. The use of an added acid is not a critical aspect of the present process.

The reaction generally is substantially complete within about forty-eight hours, although longer reaction times do not appear detrimental and can be employed if desired. The reaction typically is simply carried out overnight, for instance about twelve to about sixteen hours.

Upon completion of the process, the 3-bromo-3-methylcepham product can be conveniently isolated by routine methods. Normally, the reaction solvent is removed by evaporation under reduced pressure and the resulting product is simply purified by standard techniques such as chromatography or crystallization.

The 3-bromo-3-methylcephams prepared by the process of this invention are useful in the synthesis of cephalosporin antibiotics. For example, the 3-bromo-3-methylcephams are easily transformed to the corresponding Δ³ cephems by treatment with an inorganic or organic base such as potassium hydroxide, sodium carbonate, aliphatic or aromatic amines, quaternary alkylammonium bases, basic ion exchange resins and the like. This conversion follows the following scheme:

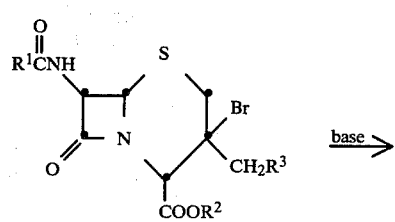

-continued

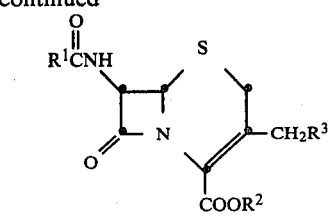

wherein R[1], R[2] and R[3] are as defined above. Removal of any protecting groups (for example R[2], the carboxy protecting group) by routine methods affords the corresponding 3-methyl-3-cephem-4-carboxylic acid or salt, i.e. the cephalosporin antibiotic. The latter compounds are well known in the art and are useful in the treatment of bacterial infections in humans and animals.

The process provided by this invention is more fully described by the working examples that follow.

EXAMPLE 1

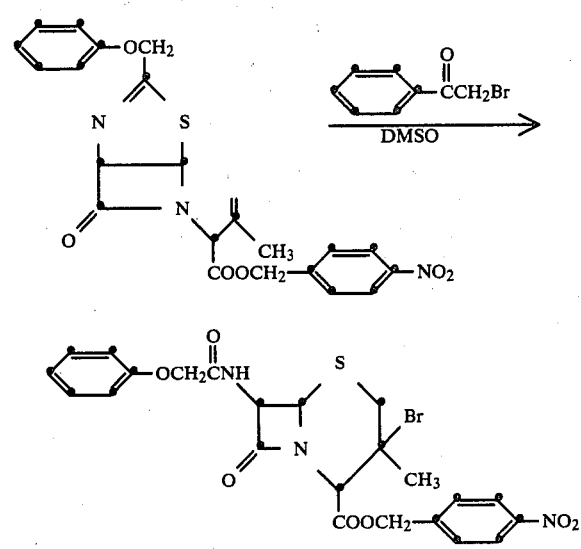

A solution of 466 mg. (1 mmole) of the thiazoline azetidinone in 5 ml. of dimethyl sulfoxide (DMSO) containing 200 mg. of benzoylmethyl bromide was stirred at 24° C. for sixteen hours. Thin layer chromatographic analysis indicated complete reaction. The solvent was removed from the reaction mixture by evaporation under reduced pressure to provide p-nitrobenzyl 7-phenoxyacetamido-3-bromo-3-methylcepham-4-carboxylate.

EXAMPLE 2

The procedure of Example 1 was repeated, except that the reaction was conducted in 10 ml. of DMSO and 1 ml. of water. Following evaporation of the solvent mixture, the product was purified by thick layer chromatography to provide 304 mg. of p-nitrobenzyl 7-phenoxyacetamido-3-bromo-3-methylacepham-4-carboxylate.

EXAMPLE 3

The procedure of Example 1 was repeated except that the reaction was carried out in the presence of 50 mg. of p-toluenesulfonic acid monohydrate. Normal isolation and purification by thick layer chromatography gave 270 mg. of p-nitrobenzyl 7-phenoxyacetamido-3-bromo-3-methylcepham-4-carboxylate.

EXAMPLE 4

The procedure of Example 3 was repeated except that the reaction was carried out over a forty hour period. Thick layer chromatography over silica gel plates, eluting with 3:1 ethyl acetate:benzene (v/v) provided, following evaporation of the solvent from the appropriate fractions, 381 mg. of p-nitrobenzyl 7-phenoxyacetamido-3-bromo-3-cepham-4-carboxylate.

EXAMPLE 5

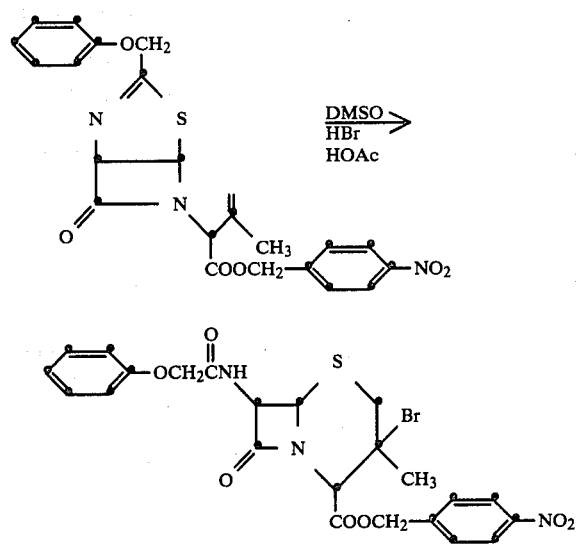

A solution of 466 mg. (1 mmole) of the thiazoline azetidinone in 5 ml. of DMSO containing 10 mg. of hydrobromic acid and 1.0 mg. of glacial acetic acid was stirred for sixteen hours at room temperature. Thin layer chromatographic analysis demonstrated that the only product was p-nitrobenzyl 7-phenoxyacetamido-3-bromo-3-methylcepham-4-carboxylate.

EXAMPLE 6

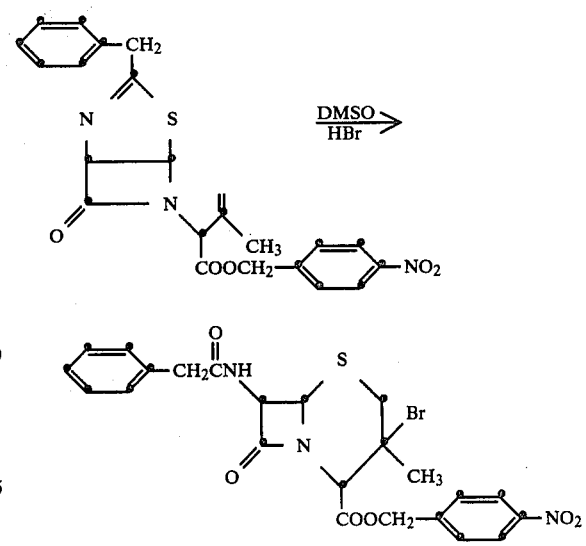

A solution of 253 mg. of the thiazoline azetidinone in 1 ml. of DMSO containing 50 mg. of 48% aqueous hydrobromic acid was stirred at 24° C. for sixteen hours. Evaporation of the reaction solvent under reduced pressure afforded 149 mg. of yellow foam identified as p-nitrobenzyl 7-phenylacetamido-3-bromo-3-methylcepham-4-carboxylate.

EXAMPLE 7

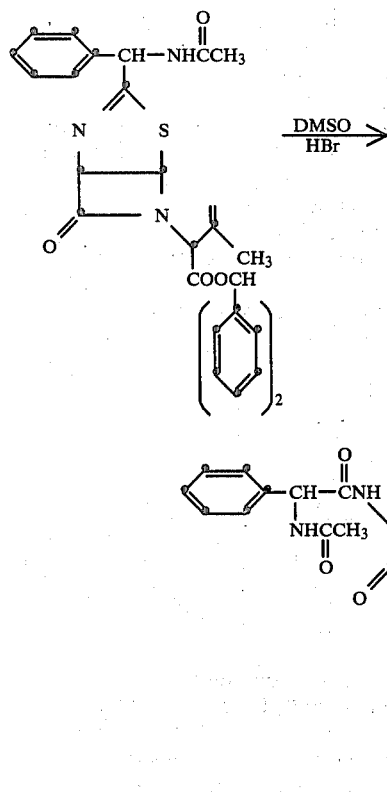

A solution of 230 mg. of the thiazoline azetidinone in 1 ml. of DMSO containing 34 mg. of 48% aqueous hydrobromic acid was stirred at room temperature for sixteen hours. Removal of the solvent by evaporation under reduced pressure provided 214 mg. that was identified as benzhydryl 7-(α-acetamido)phenylacetamido-3-bromo-3-cepham-4-carboxylate. Further purification by thick layer chromatography gave 63 mg. of the 3-bromo-3-methylcepham.

NMR (CDCl$_3$) δ 2.0 (3H, s, CH$_3$); 52.13 (s, 3H); δ 3.35 (2H); δ 4.92 (1H, s); δ 5.10 (1H, d); δ 5.44 (1H, d); δ 5.75 (H, g); δ 6.87 (1H, s); δ 7.4 (15H).

EXAMPLE 8

A solution of 120 mg. of the thiazoline azetidinone in 1 ml. of DMSO containing 0.02 ml. of 48% aqueous hydrobromic acid was stirred at 24° C. for sixteen hours to provide, following isolation by the method of Example 7, 68 mg. of cyanomethyl 7-phenoxyacetamido-3-bromo-3-methylcepham-4-carboxylate.

NMR (CDCl$_3$) δ 2.2 (3H, s, CH$_3$); δ 3.41 (2H, q); δ 4.39 (2H, s); δ 4.75 (1H, s); δ 4.83 (2H, q).

EXAMPLE 9

A solution of 190 mg. of the thiazoline azetidinone in 1 ml. of DMSO containing 0.03 ml. of 48% aqueous hydrobromic acid was stirred at room temperature for sixteen hours. The solvent was removed by evaporation under reduced pressure to give 186 mg. of 2,2,2-trichloroethyl 7-(2-thiophene)acetamido-3-bromo-3-methyl-4-carboxylate.

NMR (CDCl$_3$) δ1.98 (3H, s, CH$_3$); δ3.15 (2H, quartet); δ3.83 (2H, s); δ4.82 (2H, s); δ4.97 (1H, s); δ5.29 (1H, doublet); δ5.60 (1H, quartet); 6.8–7.3 (4H, multiplet, aromatic, NH).

EXAMPLE 10

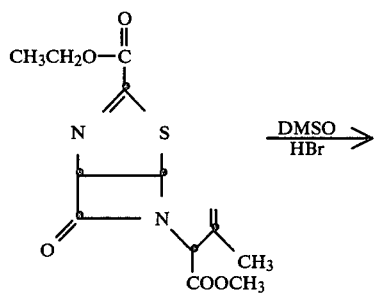

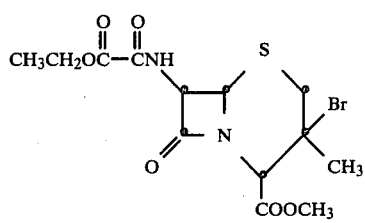

A solution of 3.12 mg. of the thiazoline azetidinone in 2 ml. of DMSO containing 0.106 ml. of 48% aqueous hydrobromic acid was stirred at room temperature for sixteen hours. Removal of the solvent by evaporation under reduced pressure gave 278 mg. of methyl 7-ethoxycarbonylformamido-3-bromo-3-methylcepham-4-carboxylate.

NMR (CDCl₃) δ1.2 (3H, triplet J=7 Hz); δ1.90 (3H, s, CH₃); δ3.22 (2H, quartet, J=15 Hz); δ3.81 (3H, s, CH₃ ester); δ4.40 (2H, quartet J=7 Hz); δ4.85 (1H, s); δ5.27 (1H, s, J=4 Hz); δ5.60 (1H, quartet); δ8.15 (1H doublet).

I claim:

1. A process for preparing a 3-bromo-3-methylcepham of the formula

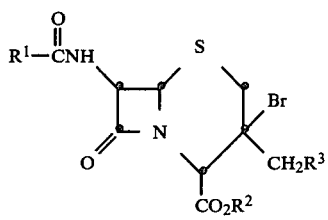

wherein:
R¹ is an organic radical;
wherein R¹ is:
(a) C₁–C₇ alkyl, cyanomethyl, C₁–C₆ haloalkyl, 4-protected amino-4-protected carboxybutyl; or
(b) C₁–C₆ alkoxy, phenoxy, benzyloxy or 4-methoxybenzyloxy; or
(c) the group —R⁴ wherein R⁴ is phenyl or substituted phenyl wherein the substitutes are 1 or 2 halogens, protected hydroxy, cyano, trifluoromethyl, C₁–C₄ alkyl, C₁–C₄ alkoxy, protected carboxy, protected carboxymethyl, protected hydroxymethyl, protected aminomethyl, or a bicyclic aryl group selected from naphthyl, benzothienyl, substituted naphthyl or substituted benzothienyl; or (d) an arylalkyl group of the formula R⁴—(O)ₘ—CH₂— wherein R⁴ is as defined above, and m is 0 or 1; or
(e) a substituted arylalkyl group of the formula

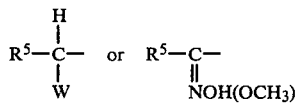

wherein R⁵ is R⁴ as defined above, 2-thienyl, 3-thienyl, 2-protected aminothiazol-4-yl, 2-furyl or 3-furyl; W is protected hydroxy, protected carboxy, protected amino, or
(f) a heteroarylmethyl group of the formula R⁶—CH₂— wherein R⁶ is 2-thienyl, 3-thienyl, 2-protected aminothiazol-4-yl, 2-furyl, 3-furyl, 2thiazolyl, 5-tetrazolyl, 1-tetrazolyl;
R² is a carboxy protecting group;
R³ is hydrogen, bromo, chloro, acetoxy, alkylthio or arylthio;
comprising reacting a thiazoline azetidinone of the formula

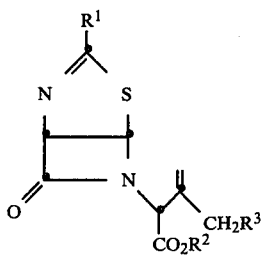

with a bromine source and dimethyl sulfoxide at a temperature of about 0° C. to about 50° C.

2. The process of claim 1 wherein R² is selected from tert.-butyl, 2,2,2-trichloroethyl, cyanomethyl, methyl, p-methoxybenzyl, diphenylmethyl, or 2,4,6-trimethylbenzyl.

3. The process of claim 2 wherein R³ is hydrogen, chloro, acetoxy,

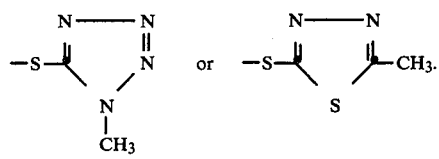

4. The process of claim 3 wherein R¹ is phenoxymethyl, 2-thiophenemethyl, ethoxycarbonyl, chloromethyl, α-acetamidophenylmethyl.

5. The process of claim 4 wherein R² is p-nitrobenzyl, 2,2,2-trichloroethyl, methyl or diphenylmethyl.

6. The process of claim 5 wherein R³ is hydrogen or chloro.

7. The process of claim 1 wherein the bromine source is aqueous hydrobromic acid.

8. The process of claim 1 wherein the bromine source is benzoylmethyl bromide.

9. The process of claim 1 wherein the bromine source is hydrobromic acid.

* * * * *